(12) United States Patent
Chang

(10) Patent No.: US 10,065,033 B2
(45) Date of Patent: *Sep. 4, 2018

(54) SYSTEM AND METHOD FOR REGULATING WATER METABOLISM OF CELLS

(71) Applicant: Wen-Chieh Chang, Taichung (TW)

(72) Inventor: Wen-Chieh Chang, Taichung (TW)

(73) Assignee: Taiwan Resonant Waves Research Corp., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/289,965

(22) Filed: Oct. 11, 2016

(65) Prior Publication Data

US 2018/0099142 A1    Apr. 12, 2018

(51) Int. Cl.
*A61N 1/32* (2006.01)
*A61N 1/04* (2006.01)

(52) U.S. Cl.
CPC ............ *A61N 1/32* (2013.01); *A61N 1/0492* (2013.01)

(58) Field of Classification Search
CPC .................................. A61N 1/32; A61N 1/0492
See application file for complete search history.

(56) References Cited

U.S. PATENT DOCUMENTS

| | | | |
|---|---|---|---|
| 2005/0249667 A1* | 11/2005 | Tuszynski | A61B 8/08 424/9.3 |
| 2007/0027483 A1* | 2/2007 | Maschino | A61N 1/36053 607/2 |
| 2017/0172842 A1* | 6/2017 | Chang | A61H 23/008 |
| 2018/0071529 A1* | 3/2018 | Chang | A61N 1/0492 |

* cited by examiner

Primary Examiner — Catherine Voorhees

(57) ABSTRACT

A system and method for regulating water metabolism of cells, which comprises an energy wave generator has an energy wave's frequency control mode. The energy wave's frequency control mode includes multiple controls for acting the energy wave generator to generate and emit energy waves each with a corresponding energy density. The energy density is calculated by a corresponding base frequency, a sweep bandwidth of the corresponding base frequency, an emission rate and a total time of emission in a duty cycle, so that the energy waves with the corresponding energy densities effecting on the body of animals or human to regulate water metabolism of cells of animals or human.

19 Claims, 5 Drawing Sheets

| Order | Fo(hz) | D(%) | P(hz) | T(sec) | SF(1) | SD(2) | SI(3) | SC(4) | SE(5) | Width | TT(sec) | ED | Norm | ED.A5 | ED.A6 | ED.A3 | Average | filter | Lower limit | Upper limit | <Lower limit | >Upper limit |
|---|---|---|---|---|---|---|---|---|---|---|---|---|---|---|---|---|---|---|---|---|---|---|
| 1 | 10000 | 70 | 1 | 45 | 1 | | | | | 0 | 45 | 5.50 | 3.2% | 5.50 | 5.62 | 5.92 | 5.68 | 1 | 4.12 | 7.03 | 2.68 | 9.18 |
| 2 | 5000 | 70 | 1 | 50 | 1 | | | | | 0 | 50 | 5.24 | 3.0% | 5.24 | 5.25 | 5.43 | 5.31 | 1 | 3.93 | 6.56 | 2.31 | 8.81 |
| 3 | 3176 | 70 | 1 | 16 | | | | 4 | | 1 | 48 | 5.51 | 3.2% | 5.51 | 5.13 | 5.27 | 5.30 | 1 | 3.84 | 6.88 | 2.30 | 8.80 |
| 4 | 3000 | 70 | 1 | 50 | 1 | | | | | 0 | 50 | 5.02 | 2.9% | 5.02 | 4.95 | 5.27 | 5.08 | 1 | 3.71 | 6.28 | 2.08 | 8.58 |
| 5 | 2128 | 70 | 1 | 120 | 1 | | | | | 0 | 120 | 5.25 | 3.0% | 5.25 | 4.57 | 5.26 | 5.03 | 1 | 3.43 | 6.57 | 2.03 | 8.53 |
| 6 | 2008 | 70 | 1 | 120 | 1 | | | | | 0 | 120 | 5.23 | 3.0% | 5.23 | 4.23 | 5.25 | 4.90 | 1 | 3.17 | 6.53 | 1.90 | 8.40 |
| 7 | 1865 | 70 | 1 | 55 | 1 | | | | | 0 | 55 | 4.86 | 2.8% | 4.86 | 4.52 | 5.23 | 4.87 | 0 | 0.00 | 0.00 | 1.87 | 8.37 |
| 8 | 1600 | 70 | 1 | 55 | 1 | | | | | 0 | 55 | 4.79 | 2.7% | 4.79 | 4.22 | 6.67 | 5.23 | 0 | 0.00 | 0.00 | 2.23 | 8.73 |
| 9 | 1550 | 70 | 1 | 18 | | 2 | | | | 2 | 54 | 5.24 | 3.0% | 5.24 | 4.21 | 6.19 | 5.21 | 0 | 0.00 | 0.00 | 2.21 | 8.71 |
| 10 | 1500 | 70 | 1 | 55 | 1 | | | | | 0 | 55 | 4.76 | 2.7% | 4.76 | 4.18 | 6.06 | 5.00 | 1 | 3.14 | 5.95 | 2.00 | 8.50 |
| 11 | 1000 | 70 | 1 | 60 | 1 | | | | | 0 | 60 | 4.62 | 2.6% | 4.62 | 4.48 | 5.18 | 4.76 | 1 | 3.36 | 5.78 | 1.76 | 8.26 |
| 12 | 880 | 70 | 1 | 65 | 1 | | | | | 0 | 65 | 4.60 | 2.6% | 4.60 | 4.14 | 5.14 | 4.63 | 1 | 3.11 | 5.75 | 1.63 | 8.13 |
| 13 | 801 | 70 | 1 | 8 | | 2 | | | | 7 | 64 | 5.46 | 3.1% | 5.46 | 4.35 | 5.13 | 4.98 | 1 | 3.26 | 6.82 | 1.98 | 8.48 |
| 14 | 787 | 70 | 1 | 70 | 1 | | | | | 0 | 70 | 4.59 | 2.6% | 4.59 | 4.13 | 5.12 | 4.61 | 1 | 3.10 | 5.73 | 1.61 | 8.11 |
| 15 | 751 | 70 | 1 | 70 | 1 | | | | | 0 | 70 | 4.57 | 2.6% | 4.57 | 4.11 | 5.05 | 4.57 | 0 | 0.00 | 0.00 | 1.57 | 8.07 |
| 16 | 727 | 70 | 1 | 35 | | 2 | | | | 1 | 70 | 4.85 | 2.8% | 4.85 | 3.60 | 4.87 | 4.44 | 0 | 0.00 | 0.00 | 1.44 | 7.94 |
| 17 | 676 | 70 | 1 | 75 | 1 | | | | | 0 | 75 | 4.55 | 2.6% | 4.55 | 3.19 | 6.10 | 4.61 | 0 | 0.00 | 0.00 | 1.61 | 8.11 |
| 18 | 650 | 70 | 1 | 75 | 1 | | | | | 0 | 75 | 4.53 | 2.6% | 4.53 | 2.87 | 5.61 | 4.34 | 0 | 0.00 | 0.00 | 1.34 | 7.84 |
| 19 | 630 | 70 | 1 | 5 | | | | 4 | | 7 | 75 | 5.70 | 3.3% | 5.70 | 2.77 | 4.79 | 4.42 | 1 | 2.08 | 7.12 | 1.42 | 7.92 |
| 20 | 598 | 70 | 1 | 15 | | | | 4 | | 2 | 75 | 5.20 | 3.0% | 5.20 | 2.74 | 4.62 | 4.18 | 1 | 2.05 | 6.49 | 1.18 | 7.68 |
| 21 | 522 | 70 | 1 | 75 | 1 | | | | | 0 | 75 | 4.44 | 2.5% | 4.44 | 2.92 | 5.53 | 4.30 | 1 | 2.19 | 5.55 | 1.30 | 7.80 |
| 22 | 2128 | 70 | 1 | 60 | 1 | | | | | 0 | 60 | 4.95 | 2.8% | 4.95 | 2.60 | 4.47 | 4.01 | 1 | 1.95 | 6.19 | 1.01 | 7.51 |
| 23 | 2008 | 70 | 1 | 60 | 1 | | | | | 0 | 60 | 4.93 | 2.8% | 4.93 | 2.55 | 4.43 | 3.97 | 0 | 0.00 | 0.00 | 0.97 | 7.47 |
| 24 | 465 | 70 | 1 | 85 | 1 | | | | | 0 | 85 | 4.44 | 2.5% | 4.44 | 2.80 | 4.39 | 3.88 | 0 | 0.00 | 0.00 | 0.88 | 7.38 |
| 25 | 442 | 70 | 1 | 18 | | | | 4 | | 2 | 90 | 5.14 | 2.9% | 5.14 | 2.32 | 4.25 | 3.90 | 0 | 0.00 | 0.00 | 0.90 | 7.40 |
| 26 | 346 | 70 | 1 | 85 | 1 | | | | | 0 | 85 | 4.31 | 2.5% | 4.31 | 3.05 | 4.13 | 3.83 | 0 | 0.00 | 0.00 | 0.83 | 7.33 |
| 27 | 304 | 70 | 1 | 90 | 1 | | | | | 0 | 90 | 4.28 | 2.5% | 4.28 | 2.23 | 3.40 | 3.30 | 0 | 0.00 | 0.00 | 0.30 | 6.80 |
| 28 | 249 | 70 | 1 | 90 | 1 | | | | | 0 | 90 | 4.20 | 2.4% | 4.20 | 2.95 | 3.23 | 3.46 | 1 | 2.21 | 5.24 | 0.46 | 6.96 |
| 29 | 147 | 70 | 1 | 18 | | | | 4 | | 2 | 90 | 4.67 | 2.7% | 4.67 | 2.17 | 0.00 | 2.28 | 1 | 1.63 | 5.83 | -0.72 | 5.78 |
| 30 | 125 | 70 | 1 | 90 | 1 | | | | | 0 | 90 | 3.90 | 2.2% | 3.90 | 2.40 | 0.00 | 2.10 | 1 | 1.80 | 4.87 | -0.90 | 5.60 |
| 31 | 95 | 70 | 1 | 100 | 1 | | | | | 0 | 100 | 3.82 | 2.2% | 3.82 | 2.03 | 0.00 | 1.95 | 0 | 0.00 | 0.00 | -1.05 | 5.45 |
| 32 | 72 | 70 | 1 | 120 | 1 | | | | | 0 | 120 | 3.78 | 2.2% | 3.78 | 0.00 | 0.00 | 1.26 | 0 | 0.00 | 0.00 | -1.74 | 4.76 |
| 33 | 33 | 70 | 1 | 20 | | 2 | | | | 7 | 160 | 4.47 | 2.6% | 4.47 | 0.00 | 0.00 | 1.49 | 0 | 0.00 | 0.00 | -1.51 | 4.99 |
| 34 | 20 | 70 | 1 | 160 | 1 | | | | | 0 | 160 | 3.35 | 1.9% | 3.35 | 0.00 | 0.00 | 1.12 | 0 | 0.00 | 0.00 | -1.88 | 4.62 |
| 35 | 10 | 70 | 1 | 15 | | | | 4 | | 5 | 165 | 4.10 | 2.4% | 4.10 | 0.00 | 0.00 | 1.37 | 0 | 0.00 | 0.00 | -1.63 | 4.87 |
| 36 | 2128 | 70 | 1 | 45 | 1 | | | | | 0 | 45 | 4.83 | 2.8% | 4.83 | 0.00 | 0.00 | 1.61 | 1 | 0.00 | 6.03 | -1.39 | 5.11 |
| 37 | 2008 | 70 | 1 | 45 | 1 | | | | | 0 | 45 | 4.80 | 2.8% | 4.80 | 0.00 | 0.00 | 1.60 | 1 | 0.00 | 6.00 | -1.40 | 5.10 |
| 38 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 39 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 40 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 41 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 42 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 43 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 44 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 45 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 46 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 47 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 48 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 49 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |
| 50 | 0 | 70 | 1 | 0 | 0 | 0 | 0 | 0 | 0 | 0 | 0 | 0.00 | 0.0% | 0.00 | 0.00 | 0.00 | 0.00 | 0 | 0.00 | 0.00 | -3.00 | 3.50 |

FIG.9

SYSTEM AND METHOD FOR REGULATING WATER METABOLISM OF CELLS

BACKGROUND OF THE INVENTION

1. Fields of the Invention

The present invention relates to a system and method for regulating water metabolism of cells, and more particularly, to a technology for controlling and emitting energy waves to regulate water metabolism function of cells of animal or human.

2. Descriptions of Related Art

Water metabolism of cells generally known is an extremely complex physiological process. The water metabolism of cell refers to the excrete process of metabolic waste and remaining water during transmission, distribution and after being used by the body. The main sources of liquid water in the body are from diet and drink, usually are through the absorption of the stomach, spleen, small intestine, large intestine and the digestive system. As for the processes of water metabolism, they are accomplished mainly by the spleen, lung and kidney. According to the theory of Traditional Chinese Medicine, once liquid water absorbed in the body, it is cleared up through the spleen firstly, then is transmitted to cardiopulmonary, meanwhile a part of unabsorbed liquid water is transmitted down to the large intestine together with food scraps and finally excreted by feces. On the other hand, the lung receives large amounts of water transmitted from the spleen and distribute throughout the body, in which part of the water is dealt by the lungs and stomach and then run to the whole body so as to moisturize the cells of skin and muscle. After metabolic, the waste and residual water are transpired and converted to be sweat, and excreted out of the body through the pores. Another part of liquid water is driven by the heart from the lungs, and runs through the whole body along the meridians to reach internal organs, joints and brain, and is gathered in the kidneys after used by the organs. In addition, the movement of the breath in the lungs can discharge a small amount of water vapor, according to the theory of Traditional Chinese medicine, the water accumulated in the kidney organ under the gasification of the kidney is secreted into the clear and muddy parts, which part of clear liquid water return to the lungs through the transpiration and gasification effect of the kidney, then spread in the body through the lungs and heart to maintain the body with normal quantity of liquid water. As to the part of muddy water in the kidney, it is converted to be urine and transported down to the bladder. When the urine in the bladder is accumulated to a certain amount, the body recognizes autonomously it should excrete urine through the urethra. It can be seen, normal cell metabolism of liquid water or not is at stake with the normal function of the five internal organs system. Therefore, in the process of water metabolism in cells, the physiological function of the internal organs is really needed in order so as to effectively complete the function of water metabolism of cells.

Once one of the three organs, spleen, lung and kidney has dysfunction, obstacles of excretion of liquid water will produce, which result in abnormal moisture stayed in the body and produce pathological phenomena such as phlegm and edema. Theoretical Chinese medicine assumes that the sputum is pathological product formed because of metabolism obstacle of water, liquid and fluid in the body. When liquid water running, transmitting and converting disorder, the moisture will abnormally stay in the body and become sputum. Chinese medicine also believes phlegm has narrow, broad, visible and invisible points. According to narrow point, phlegm is exudate of lungs and respiratory secretions. According to broad point, phlegm is pathological product, variated process of disease and symptom caused by cell's water metabolism disorder. According to visible point, phlegm is usually visible coughed up sputum, as it refers to the invisible point, invisible phlegm is variety of symptoms and body signs due to phlegm effect, such as heart palpitations, shortness of breath, nausea, vomiting and other pathological phenomena. Constitution of phlegm body is due to liquid water stop and phlegm cohesion, which forms a main feature of viscous muddy. Furthermore, although the five internal organs dysfunction will result with phlegm, but the most important factor is disorder of the spleen and kidney. The spleen deals with wet in the body, if the wet in the body is not dislodged will result to form phlegm. The kidney deals with water in the body, if the water metabolism is disordered also will result to form phlegm. Therefore, in view of Chinese medicine, in order to treat phlegm constitution, it is suggested to select appropriate foods or herbal medicines to improve the function of spleen.

To apply wave energy in sound, electromagnetic or optical form effecting on plant, animal or human, to promote cell growth, or inhibit the growth of foreign cells, or produce specific physiological or psychological treatment or soothing, is currently quite universally endorsed technology and research. But currently available conventional arts are only roughly using energy wave emitted by simple combination of low and high frequencies to act on the human body, they are not in-depth studied to know and have what kind combination of energy waves emitted in specific different frequencies is effective for corresponding diseases and physical discomfort, and they are energy waves only in rough frequencies regardless what kind illness or physical discomfort to be suitably applied for, so the effectiveness of treatment or relieve of symptoms of diseases must be unable to highlight.

Since the biological resonant waves probably have high efficacy in improvement of physiological faculty and curing diseases, and the inventor of the present patent application has researched for a long time to apply the resonant energy wave to improve some kinds of physiological faculty and cure some diseases. The inventor had an invention of system and method for emitting energy wave by specific frequency controls to reduce or eliminate high blood sugar factor of diabetes, and such invention had been issued for Taiwanese patent No. 1453046 and U.S. Pat. No. 9,421,368. After the aforementioned invention, the inventor of the present patent application puts into research applying serial specific controls of energy wave to improve the symptoms of disease such as the present invention for regulating water metabolism function of cells of animal or human.

SUMMARY OF THE INVENTION

The primary objective of the present invention is to provide a system and method for regulating water metabolism function of cells of animal or human. The system comprises an energy wave generator including an energy wave's frequency control mode for controlling and generating energy waves. The energy wave's frequency control mode comprises multiple controls in multiple energy wave generation periods respectively. According to the multiple controls, the energy wave generator generates and emits energy waves each with a corresponding energy density having a value between 0.00~7.12 by a corresponding base frequency between 100~10100 Hz to effect on bodies of animals or human so as to regulate water metabolism function of cells of the animals or human. The control modes are at least one fixed frequency sweep mode and at least one adjusted frequency sweep mode. The energy density of each energy wave is calculated by the following formula: ED=log 10 (freq.×D %×(2Width+1)×(TT)+1), wherein freq., Width, D % and TT represent the base frequency, the predetermined sweep bandwidth, an emission rate and a total time of emission in a duty cycle of the base frequency respectively.

BRIEF DESCRIPTION OF THE DRAWINGS

FIG. 9 is a schematic view of list of relations between spectrums of effect frequencies, modulation parameters and energy densities of the present invention.

DETAILED DESCRIPTION OF THE PREFERRED EMBODIMENT

Referring to FIGS. 1 to 6, the system of the present invention comprises an energy wave generator 10. The energy wave generator 10 is set up with an energy wave's frequency control mode. The energy wave generator 10 generates and emits energy waves (i.e. resonant wave) according to the control of the energy wave's frequency control mode. In one embodiment of the present invention, the energy wave's frequency control mode includes first to fifth sets of controls in corresponding first to fifth sets of energy wave generation periods. The energy wave generator 10 generates and emits the energy waves each with a corresponding energy density by a corresponding frequency sweep mode based on a base frequency in the first to fifth energy wave generation periods respectively according to the controls of the energy wave's frequency control mode, so that the energy waves effect on the body of animal or human to regulate water metabolism function of cells of animals or human.

Figure 1:
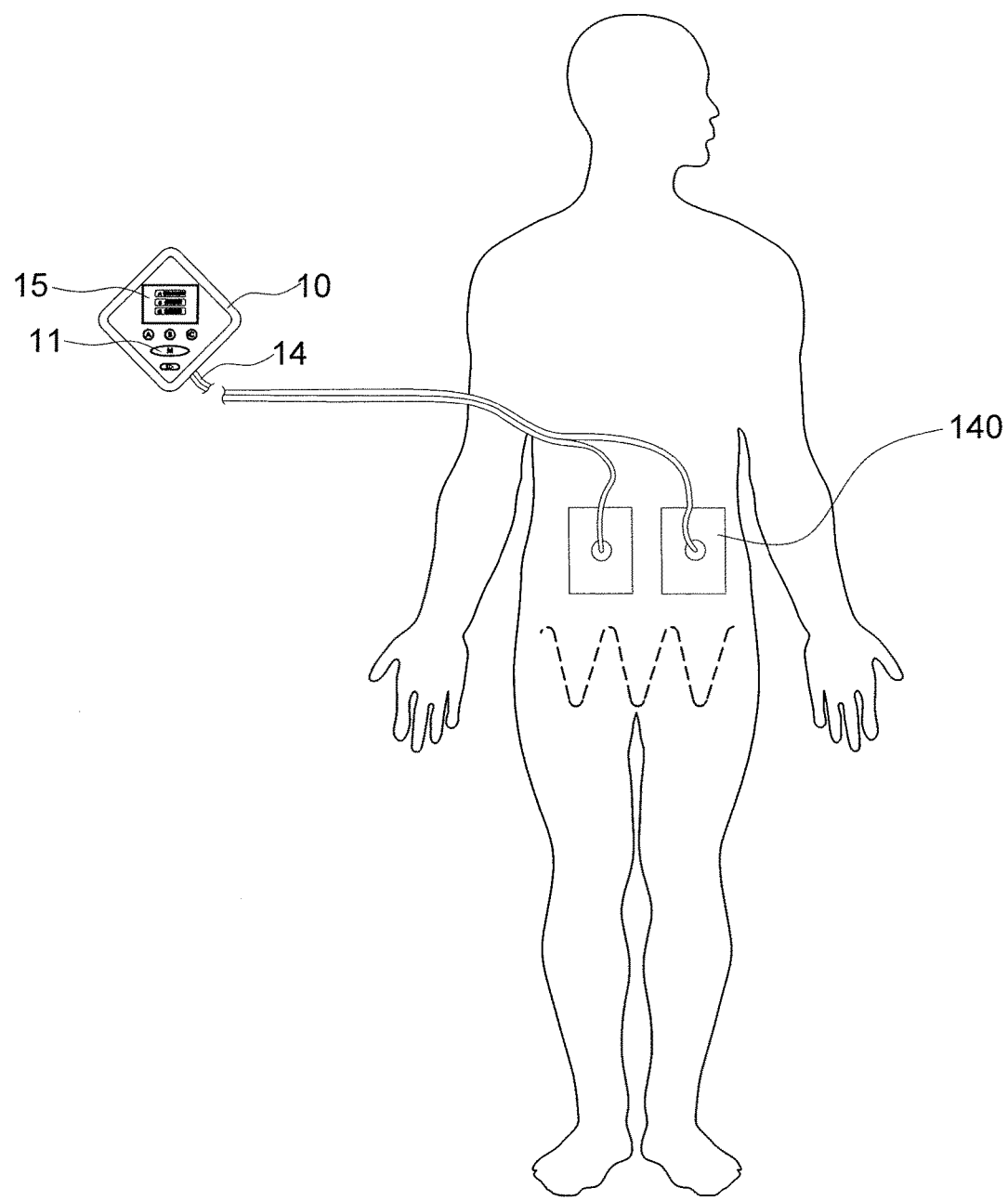
FIG. 1 is a schematic view of the system of the present invention.
Figure 2:
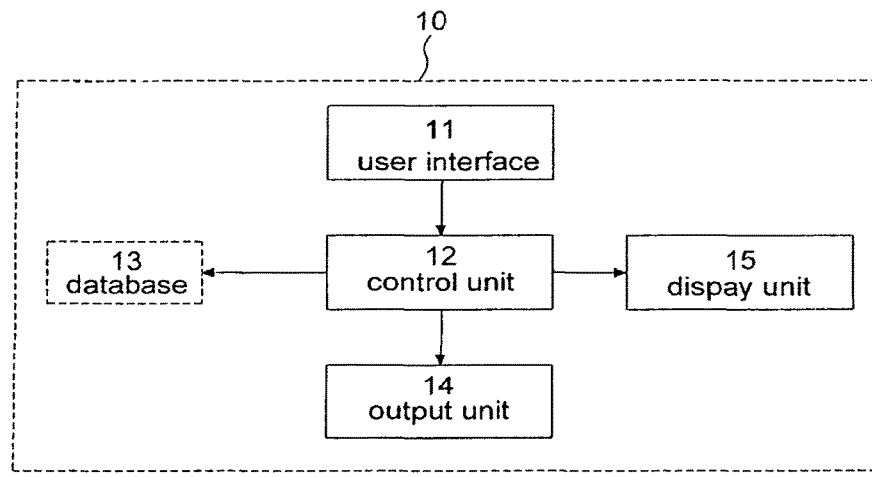
FIG. 2 is a schematic block diagram of units of the system of the present invention.

Referring to FIGS. 1 to 2, the energy wave generator 10 comprises a user interface 11, a control unit 12, a database 13 for saving the information of spectrums of effect frequency and modulation parameters corresponding to each effect frequency used in each energy wave generation periods, an energy wave output unit 14 and a display unit 15. In one embodiment of the present invention, the energy waves are in electric forms, and the energy wave output unit 14 includes a set of electrode sheets 140 for affixing to the body of animal or human so as to construct a circulation loop between the body and the electrical energy wave output unit 14 to transmit electric energy waves to the body of animal or human. The control unit 12 (such as a combination of microcontroller and driving circuit) sequentially reads the information of spectrums and modulation parameters of effect frequencies in the database 13, and then drives the energy wave output unit 14 to sequentially generates and emits electric energy waves each with a respective energy density (ED) in each corresponding energy wave generation period.

The control unit 12 of the present invention can be triggered to read the associated information of spectrums and modulation parameters in the database 13 by the command signals generated from the user interface 11, and then generates driving signals to control the energy wave output unit 14 (such as weak pulse generating circuit, voltage 10V, current 5 mA) switching on and off according to the corresponding frequencies, so that the energy wave output unit 14 generates corresponding electric energy waves with corresponding energy densities in required distributions of values in the corresponding energy wave generation periods. The display unit 15 is used to display the status of operation or procession of the system. Further, the embodiment of the present invention, the energy wave output unit 14 is not to be limited to a weak pulse generating circuit, the energy wave output unit 14 also may be a light emitting device or an audio play device enabling the energy wave generator system 10 to emits energy waves in light form or audio form in required corresponding frequencies.

Referring to FIG. 9, in one embodiment of the invention, the energy wave generator 10 according to the control of the energy wave's frequency control mode sequentially outputs the energy waves from first to fifth energy wave generation periods. The controls of the energy wave's frequency control mode are for: (a) continuously and sequentially generating a 1st to a 6th energy waves with a corresponding 1st to a 6th energy densities by a corresponding 1st to a 6th base frequencies respectively in the first energy wave generation period, wherein, the 1st energy density of the 1st energy wave is between 4.12~7.03 (preferably 5.50), the 2nd energy density of the 2nd energy wave is between 3.93~6.56 (preferably 5.24), the 3rd energy density of the 3rd energy wave is between 3.84~6.88 (preferably 5.51), the 4th energy density of the 4th energy wave is between 3.71~6.28 (preferably 5.02), the 5th energy density of the 5th energy wave is between 3.43~6.57 (preferably 5.25) and the 6th energy density of the 6th energy wave is between 3.17~6.53 (preferably 5.23); (b) continuously and sequentially generating a 7th to a 11th energy waves with corresponding a 7th to a 11th energy densities by a 7th to a 11th base frequencies respectively in the second energy wave generation period, wherein, the 7th energy density is between 3.14~5.95 (preferably 4.76), the 8th energy density between 3.36~5.78 (preferably 4.62), the 9th energy density is between 3.11~5.75 (preferably 4.60), the 10th energy density is between 3.26~6.82 (preferably 5.46) and the 11th energy density is between 3.10~5.73 (preferably 4.59); (c) continuously and sequentially generating a 12th to a 15th energy waves with a 12th to a 15th energy densities by a 12th to a 15th base frequencies respectively in the third energy wave generation period, wherein, the 12th energy density is between 2.08~7.12 (preferably 5.70), the 13th energy density is between 2.05~6.49 (preferably 5.20), the 14th energy density is between 2.19~5.55 (preferably 4.44) and the 15th energy density is between 1.95~6.19 (preferably 4.95); (d)

continuously and sequentially generating a 16th to a 18th energy waves with a 16th to a 18th energy densities by a 16th to a 18th base frequencies respectively in the fourth energy wave generation period, wherein, the 16th energy density is between 2.21~5.24 (preferably 4.20), the 17th energy density is between 1.63~5.83 (preferably 4.67) and the 18th energy density is between 1.80~4.87 (preferably 3.90); (e) continuously and sequentially generating a 19th to a 20th energy waves with a 19th to a 20th energy densities by a 19th to a 20th base frequencies respectively in the fifth energy wave generation period, wherein, the 19th energy density is between 0.00~6.03 (preferably 4.83) and the 20th energy density is between 0.00~6.00 (preferably 4.80).

The value of aforementioned energy densities of the energy waves by their corresponding frequencies are calculated by the formula: ED=log 10 (base freq.×D %×(2Width+1)×(TT)+1). For example of the 1st base frequency in the first energy wave generation period, if we set the 1st base freq.=10000 Hz, the emission rate in a duty cycle (D %)=70%, the sweep bandwidth (Width) (m)=0 Hz and the total time of emission (TT)=45 secs in a duty cycle, and then the energy density (ED)=log 10 (10000×70%×(2×0+1)×45+1)=5.50. Although there is no specific unit referring to the energy density (ED) of the present invention, the ED has real meaning, which represents a total transmit power of energy wave. When the frequency is higher, the times of switch voltage (current) is more, and energy used is more. The total time of emission means the duration of effect energy wave. The value of ED has been taken into account with all transmission parameters, which is on behalf of transmitting behavior. If each parameter is changed too large, the ED will also change. If the energy density exceeds the scope of the set ones, the efficiency also will be changed with it.

Figure 3:
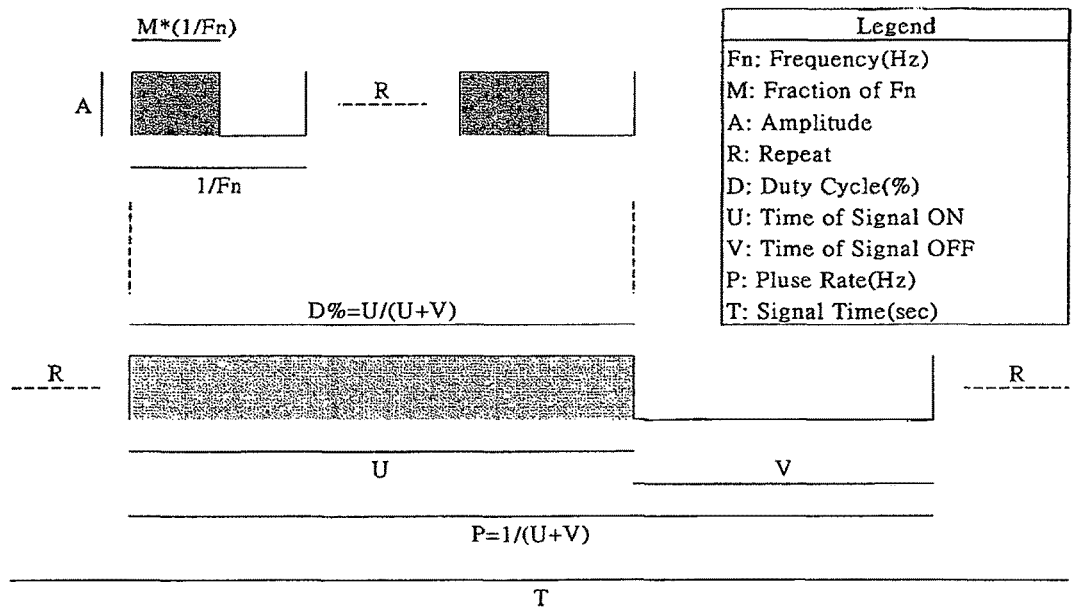
FIG. 3 is a schematic view of wave form of a duty cycle of the present invention.

As shown in FIGS. 3 and 9, in one embodiment of the present invention, the energy wave is a square wave, D is the duty cycle, T is effect time of a single frequency, D % is emission rate of duty cycle of each base frequency and equal to U/(U+V). In the embodiment of present invention, we set the wave emission rate to be 70% for each duty cycle. U is the part of 70% which represents the time of signal outputs of positive potential in square wave, and V is the part of 30% which represents the time of signal outputs of 0 potential in OFF status. P represents a Pulse Rate (Hz) of frequency, P=1/(U+V). TT is the total time of emission period based on each base frequency in each duty cycle. In FIG. 9, the normalized percentages (normal) in each order, is the ratio between the ED in the effect period based on each base frequency and the sum of ED of the whole effect periods based on whole base frequencies from order 1 to 50 shown in FIG. 9.

Referring to FIG. 9, during the first energy wave generation period, the control mode of the 1st frequency is fixed frequency sweep mode, which sets a fixed 1st base frequency within 9000~10100 Hz (preferably 10000), emission rate (D %)=70% for a duty cycle, sweep bandwidth (Width) (m)=0 Hz and total time of emission (TT)=45 seconds for a duty cycle; the control mode of the 2nd frequency is fixed frequency sweep mode, which sets a fixed 2nd base frequency within 4900~5100 Hz (preferably 5000), D %=70%, Width (m)=0 Hz and TT=50 secs for a duty cycle; the control mode of the 3rd frequency is frequency spread contract mode, which sets effect frequencies decreasing and increasing alternately adjusted to contract based on 3rd base frequency between 3100~3250 Hz (preferably 3176), D %=70%, Width (m)=1 Hz, adjusted bandwidth=1 Hz and TT=48 secs for a duty cycle; and the control mode of the 4th frequency is fixed frequency sweep mode, which sets a fixed 4th base frequency within 2900~3100 Hz (preferably 3000), D %=70%, Width (m)=0 Hz and TT=50 secs for a duty cycle; the control mode of the 5th frequency is fixed frequency sweep mode, which sets a fixed 5th base frequency within 2060~2200 Hz (preferably 2128), D %=70%, Width (m)=0 Hz and TT=120 secs for a duty cycle; and the control mode of the 6th frequency is fixed frequency sweep mode, which sets a 6th base frequency between 1950~2050 Hz (preferably 2008) with D %=70%, Width=0 Hz and TT=120 secs for a duty cycle.

Referring to FIG. 9, during the second energy wave generation period, the control mode of the 7th frequency is fixed frequency sweep mode, which sets a fixed 7th base frequency between 1400~1600 Hz (preferably 1500 Hz), D %=70%, Width=0 Hz and TT=55 seconds for a duty cycle; the control mode of the 8th frequency is fixed frequency sweep mode, which sets a fixed 8th base frequency between 950~1100 Hz (preferably 1000 Hz), D %=70%, Width=0 Hz and TT=60 secs for a duty cycle; the control mode of the 9th frequency is fixed frequency sweep mode, which sets a fixed 9th base frequency between 850~900 Hz (preferably 880 Hz), D %=70%, Width=0 Hz and TT=65 secs for a duty cycle; and the control mode of the 10th frequency is frequency sweep decreasing mode, which sets effect frequencies decreasingly adjusted and based on 10th base frequency between 750~850 Hz (preferably 801 Hz), D %=70%, Width=7 Hz, adjusted bandwidth equal to 1 Hz and TT=64 secs for a duty cycle; and the control mode of the 11th frequency is fixed frequency sweep mode, which sets a fixed 11th base frequency between 750~830 Hz (preferably 787 Hz) with D %=70%, Width=0 Hz and TT=70 secs for a duty cycle.

Referring to FIG. 9, during the third energy wave generation period, the control mode of the 12th frequency is a frequency spread contract mode, which sets effect frequencies decreasing and increasing alternately adjusted to contract based on a 12th base frequency between 615~650 Hz (preferably 630 Hz) with D %=70%, Width (m)=7 Hz, adjusted bandwidth equal to 1 Hz and TT=75 secs for a duty cycle; the control mode of the 13th frequency is a frequency spread contract mode, which sets effect frequencies decreasing and increasing alternately adjusted to contract based on a 13th base frequency between 560~610 Hz (preferably 598 Hz) with D %=70%, Width=2 Hz, adjusted bandwidth equal to 1 Hz, and TT=75 seconds for a duty cycle; the control mode of the 14th frequency is a fixed frequency sweep mode, which sets a fixed 14th base frequency between 500~550 Hz (preferably 522 Hz) with D %=70%, Width=0 Hz and TT=75 secs for a duty cycle; the control mode of the 15th frequency is a fixed frequency sweep mode, which sets a fixed 15th base frequency between 2060~2200 Hz (preferably 442 Hz) with D %=70%, Width=0 Hz and TT=60 secs for a duty cycle.

Referring to FIG. 9, during the fourth energy wave generation period, the control mode of the 16th frequency is a fixed frequency sweep mode, which sets a fixed 16th base frequency between 220~270 Hz (preferably 249 Hz) with D %=70%, Width=0 Hz and TT=90 secs for a duty cycle; the control mode of the 17th frequency is a frequency spread contract mode, which sets effect frequencies decreasing and increasing alternately adjusted to contract based on a 17th base frequency between 125~170 Hz (preferably 147 Hz) with D %=70%, Width (m)=2 Hz, adjusted bandwidth=1 Hz and TT=90 secs for a duty cycle; the control mode of the 18th frequency is a fixed frequency sweep mode, which sets a fixed 18th base frequency between 100~150 Hz (preferably 125 Hz) with D %=70%, Width=0 Hz and TT=90 secs for a duty cycle.

Referring to FIG. 9, during the fifth energy wave generation period, the control mode of the 19th frequency is a fixed frequency sweep mode, which sets a fixed 19th base frequency between 2060~2200 Hz (preferably 2128 Hz) with D %=70%, Width=0 Hz and TT=45 secs for a duty cycle; the control mode of the 20th frequency is a fixed frequency sweep mode, which sets a fixed 20th base frequency between 1950~2050 Hz (preferably 2008 Hz) with D %=70%, Width=0 Hz and TT=45 secs for a duty cycle.

Referring to FIG. 9, the control mode of the fixed frequency sweep mode depicted in the present invention means the frequency of each treatment functioning at a fixed frequency until the total time (TT) of the base frequency effect period ends. In the case of the first energy wave generation period, for example, assuming that the first frequency is 10000 Hz, then the first frequency is fixed at 10000 Hz until the total time of the frequency reaches 45 seconds. After that, it goes to the next base frequency effect period, and so on. Because there is no value change of the frequency range for the fixed frequency sweep mode, therefore, the sweep bandwidth is 0 Hz.

Figure 4:
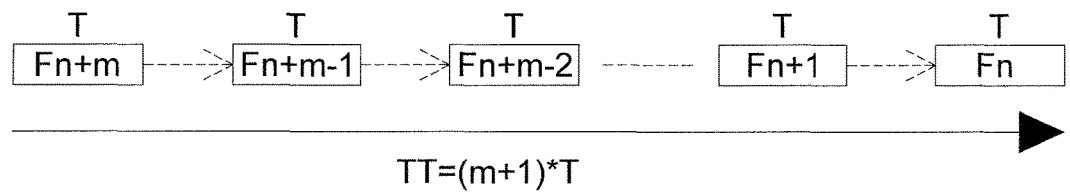
FIG. 4 is a schematic view of distribution of effect frequencies calculated by the sweep decreasing mode of the present invention.

Referring to FIGS. 4 and 9, the control mode of the aforementioned frequency sweep decreasing mode is to control the system to emit the energy wave by frequency decreasing distribution with an adjusted bandwidth in the predetermined sweep bandwidth. The calculation of the value change of the sweep decreasing mode depicted in the present invention is described as below. The first output frequency is calculated as a base frequency ($F_n$) plus a sweep bandwidth (m), and the second output frequency is calculated as the first output frequency minus an adjusted bandwidth (such as 1 Hz). When the current output frequency is equal to the base frequency ($F_n$), the current output frequency will be the last output frequency. In the case of the 10th base frequency, for example, the base frequency is 801 Hz with sweep bandwidth (Width) (m) 7 Hz. Based on the above formula, eight frequencies can be obtained, and the sequence of the output effect frequencies are 808 Hz, 807 Hz, 806 Hz, 805 Hz, 804 Hz, 803 Hz, 802 Hz and 801 Hz respectively. Each single-frequency's effect time (T) in the sweep decreasing mode is 8 seconds, so the total time of the two frequencies (TT) is 64 seconds, i.e., TT=(m+1)*T.

Figure 5:
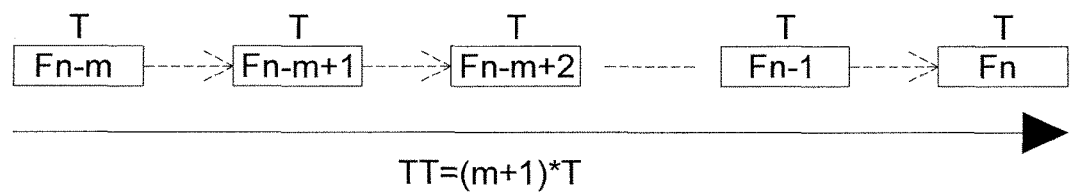
FIG. 5 is a schematic view of distribution of effect frequencies calculated by the sweep increasing mode of the present invention.

Referring to FIGS. 5 and 9, the control mode of the aforementioned frequency sweep increasing mode is to control the system to emit the energy wave by frequency increasing distribution with an adjusted bandwidth in a predetermined sweep bandwidth. The calculation of the value change of the sweep increasing mode depicted in the present invention is described as below. The first output frequency is calculated as a base frequency ($F_n$) minus the sweep bandwidth (m), and the second output frequency is calculated as the first output frequency plus an adjusted bandwidth (such as 1 Hz). When the current output frequency is equal to the base frequency ($F_n$), the current output frequency will be the last output frequency. For example, the base frequency is 3175 Hz with the sweep bandwidth (Width)=2 Hz and the adjusted bandwidth=1 Hz. Based on the above formula, three frequencies can be obtained, and the sequence of the output effect frequencies are 3173 Hz, 3174 Hz and 3175 Hz respectively. Each single-frequency's effect time (T) in the sweep increasing mode is 9 seconds, so that the total time of the three effect frequencies (TT) is 27 seconds, i.e., TT=(m+1)*T.

Figure 6:
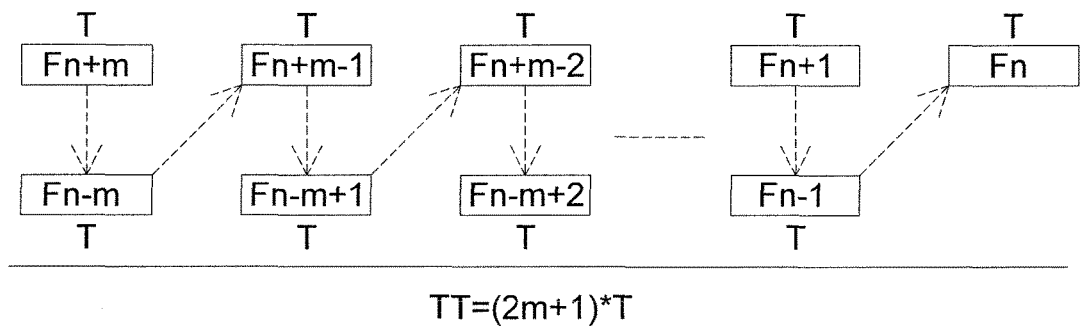
FIG. 6 is a schematic view of distribution of effect frequencies calculated by the spread contract mode of the present invention.

Referring to FIGS. 6 and 9, the control mode of the aforementioned frequency spread contract mode is to control the system to emit the energy wave by alternating increasing frequency and decreasing frequency distribution with an adjusted bandwidth in a predetermined sweep bandwidth. The calculation of the value change of the spread contract mode depicted in the present invention is described as below. The first output frequency is calculated as a base frequency ($F_n$) minus a sweep bandwidth (m), the second output frequency is calculated as a base frequency ($F_n$) plus a sweep bandwidth (m), the third output frequency is calculated as the first output frequency plus an adjusted bandwidth (such as 1 Hz), the fourth output frequency is calculated as the second output frequency minus an adjusted bandwidth (such as 1 Hz), and so on. When the current output frequency is equal to the base frequency ($F_n$), the current output frequency will be the last output frequency. In the case of the 16th base frequency, for example, the 3rd base frequency is 3176 Hz with the sweep bandwidth (m)=1 Hz and the adjusted bandwidth=1 Hz. Based on the above formula, three frequencies can be obtained, and the sequence of the output effect frequencies are 3177 Hz, 3175 Hz and 3176 Hz respectively. Each single-frequency's effect time (T) is 16 seconds, so that the total time of the fifteen frequencies (TT) is 48 seconds, i.e., TT=(2 m+1)*T.

Figure 7:
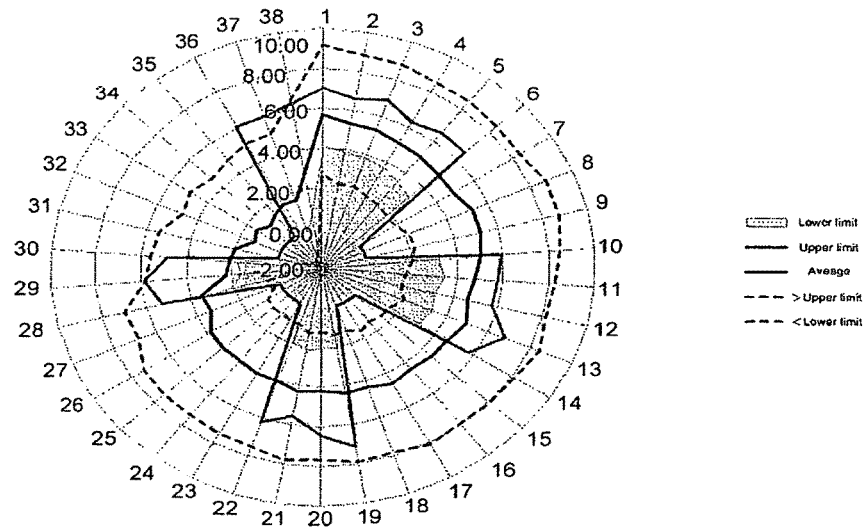
FIG. 7 is a schematic view of distribution of energy density on linear timeline of the present invention.
Figure 8:
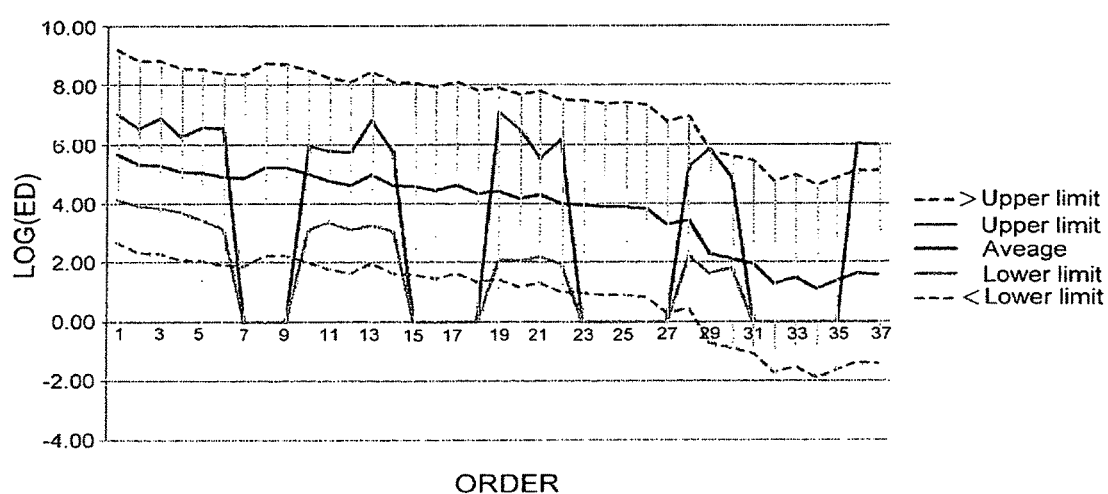
FIG. 8 is a schematic view of distribution of energy density on circular timeline of the present invention.

FIG. 7 shows the distribution schematic of the energy density in energy wave's frequency control mode against the linear timeline in the present invention. Wherein, the upper limit and the lower limit shown in FIG. 7 represent the upper range and the lower range of the energy density against the timeline mentioned above in accordance with the present invention. FIG. 8 shows the distribution schematic of the energy density in energy wave's frequency control mode against the annular timeline in the present invention. Wherein, the central portion is the average distribution of the energy density against the timeline mentioned above in accordance with the present invention.

On the chart shown in FIG. 9, the base frequency distributions of first to fifth energy wave generation periods are from orders 1-6, 10-14, 19-22, 28-30 and 36-37 chronologically respectively.

In the present embodiment, besides above frequency treatment period, the energy wave's frequency control mode also includes four non-energy periods, i.e., from the first to the fourth non-energy periods generated between every two adjacent energy density from the first to the ninth periods correspondingly. The total time of the first to fourth non-energy periods are 164, 290, 410 and 705 seconds respectively. The energy wave generator 10 generates various frequencies in each non-energy periods and filters the frequency to have non-energy. Referring to FIG. 9, the first to the eighth non-energy periods is chronologically generated in-between order 7-9, order 15-18, order 23-27 and order 31-35 in sequence.

While we have shown and described the embodiment in accordance with the present invention, it should be clear to those skilled in the art that further embodiments may be made without departing from the scope of the present invention.

What is claimed is:

1. A system for regulating water metabolism function of cells of the animals or human, comprising an energy wave generator including an energy wave's frequency control mode for controlling and generating energy waves; the energy wave's frequency control mode comprising multiple controls in multiple energy wave generation periods respectively; according to the multiple controls, the energy wave generator generating and emitting energy waves each with a corresponding energy density having a value between 0.00~7.12 by a corresponding base frequency between 100~10100 Hz to effect on bodies of animals or human so as to regulate water metabolism function of cells of the animals or human; the energy wave's frequency control mode comprising at least one fixed frequency sweep mode and at least one adjusted frequency sweep mode; the at least one adjusted frequency sweep mode being at least one sweep decreasing mode, at least one spread contract mode and/or at least one sweep increasing mode; the energy wave generator emitting energy waves to have a frequency decreasing distribution in a predetermined sweep bandwidth by a predetermined adjusted bandwidth in the sweep decreasing mode, to have a frequency increasing distribution in a predetermined sweep bandwidth by a predetermined adjusted bandwidth in the sweep increasing mode, and to have an increasing frequency and a decreasing frequency alternately in a predetermined sweep bandwidth by a predetermined adjusted bandwidth in the spread contract mode; the energy density of each energy wave being calculated by the following formula: ED=log 10 (freq.×D %×(2Width+1)×(TT)+1), wherein freq., Width, D % and TT represent the base frequency, the predetermined sweep bandwidth, an emission rate and a total time of emission in a duty cycle of the base frequency respectively.

2. The system as claimed in claim 1, wherein there is at least one non-energy period between every two adjacent periods of the multiple energy wave generation periods, the energy wave generator generates at least one base frequency in each non-energy period and filters the at least one base frequency to have non-energy.

3. The system as claimed in claim 1, wherein according to the multiple controls, the energy wave generator in two energy wave generation periods sequentially outputs two sets of energy waves with corresponding two sets of energy densities between 3.17~7.03 and 1.63~5.83 respectively.

4. The system as claimed in claim 3, wherein the D %=70%, the Width is 0, 1 or 2 Hz, and the TT=45, 48, 50, 90 or 120 secs; the base frequencies are between 9000~10100 Hz, 4900~5100 Hz, 3100~3250 Hz, 2900~3100 Hz, 2060~2200 Hz, 1950~2050 Hz, 220~270 Hz, 125~170 Hz or 100~150 Hz.

5. The system as claimed in claim 1, wherein according to the multiple controls, the energy wave generator in the multiple energy wave generation periods atoll sequentially outputs multiple sets of energy waves with corresponding multiple sets of energy densities between 4.12~7.03, 1.95~7.12 and 0.00~6.03 respectively.

6. The system as claimed in claim 5, wherein the D %=70%, the Width is 0, 1, 2 or 7 Hz, and the TT=45, 48, 50, 60, 75 or 120 secs; the base frequencies are between 9000~10100 Hz, 4900~5100 Hz, 3100~3250 Hz, 2900~3100 Hz, 2060~22001 Hz, 1950~2050 Hz, 2060~2200 Hz or 1950~2050 Hz respectively.

7. The system as claimed in claim 1, wherein the multiple controls are five sets, the multiple energy wave generation periods are five sequentially from a 1st to fifth corresponding to the five sets of controls; according to the five sets of controls, the energy wave generator sequentially emit five sets of energy waves from a 1st to fifth with corresponding five sets of energy densities between 3.17~7.03, 3.10~6.82, 1.95~7.12, 1.63~5.83 and 0.00~6.03 respectively.

8. The system as claimed in claim 7, wherein there are four non-energy periods from a first to an fourth non-energy periods sequentially between every two adjacent periods of the multiple energy wave generation periods, the energy wave generator generates various frequencies in each non-energy period and filters the various frequencies to have non-energy correspondingly.

9. The system as claimed in claim 8, wherein the total time of the first to fifth non-energy periods are 164, 290, 410 and 705 seconds respectively, the energy wave generator generates various frequencies in each non-energy period and filters the various frequencies to have non-energy.

10. The system as claimed in claim 7, wherein in the first energy wave generation period corresponding to the first set of controls, the first set of energy waves are sequentially a 1st to a 6th energy waves with a 1st to a 6th energy densities by a 1st to a 6th base frequencies respectively, the 1st energy density is between 4.12~7.03, the 2nd energy density is between 3.93~6.56, the 3rd energy density is between 3.84~6.88, the 4th energy density is between 3.71~6.28, and the 5th energy density is between 3.43~6.57, and the 6th energy density is between 3.17~6.53; in the second energy wave generation period corresponding to the second set of controls, the second set of energy waves are sequentially a 7th to a 11th energy waves with corresponding a 7th to a 11th energy densities by a 7th to a 11th base frequencies respectively, the 7th energy density is between 3.14~5.95, the 8th energy density is between 3.36~5.78, the 9th energy density is between 3.11~5.75, the 10th energy density is between 3.26~6.82, the 11th energy density is between 3.10~5.73; in the third energy wave generation period corresponding to the third set of controls, the third set of energy waves are sequentially a 12th to a 15th energy waves with a 12th to a 15th energy densities by a 12th to a 15th base frequencies respectively, the 12th energy density is between 2.08~7.12, the 13th energy density is between 2.05~6.49, the 14th energy density is between 2.19~5.55, the 15th energy density is between 1.95~6.19; in the fourth energy wave generation period corresponding to the fourth set of controls, the fourth set of energy waves are sequentially a 16th to a 19th energy waves with a 16th to a 19th energy densities by a 16th to a 19th base frequencies respectively, the 16th energy density is between 2.21~5.24, the 17th energy density is between 1.63~5.83, the 18th energy density is between 1.80~4.87; in the fifth energy wave generation period corresponding to the fifth set of controls, the fifth set of energy waves are sequentially a 19th to a 20th energy waves with a 19th to a 20th energy densities by a 19th to a 20th base frequencies respectively, the 19th energy density is between 0.00~6.03, the 20th energy density is between 0.00~6.00.

11. The system as claimed in claim 10, wherein the controls based on the 1st, 2nd, 4th to 9th, 11th, 12th, 14th to 16th and 18th to 20th base frequencies are fixed frequency sweep modes respectively, the D %=70%, the Width=0 Hz, and the TT=45, 50, 50, 120, 120, 55, 60, 65, 70, 75, 60, 90, 90, 45 and 45 secs respectively; the control based on the 10th base frequency is sweep decreasing modes, the D %=70%, the Width=7 Hz, and the TT=64 secs respectively; the controls based on the 3rd, 12th, 13th and 17th base frequencies are spread contract modes respectively, the D %=70%, the Width=1, 7, 7 and 2 Hz, and the TT=48, 75, 75 and 90 secs respectively; the 1st to 20th base frequencies are between 9000~10100 Hz, 4900~5100 Hz, 3100~3250 Hz, 2900~3100 Hz, 2060~2200 Hz, 1950~2050 Hz, 1400~1600 Hz, 950~1100 Hz, 850~900 Hz, 750~850 Hz, 750~830 Hz, 615~650 Hz, 560~610 Hz, 500~550 Hz, 2060~2200 Hz, 220~270 Hz, 125~170 Hz, 100~150 Hz, 2060~2200 Hz and 1950~2050 Hz, respectively.

12. The system as claimed in claim 1, wherein multiple effect frequencies are produced and calculated by one predetermined adjusted bandwidth equal to 1 Hz based on each base frequency in each sweep decreasing mode; multiple effect frequencies are produced and calculated by one predetermined adjusted bandwidth equal to 1 Hz based on each base frequency in each spread contract mode; multiple frequencies are produced and calculated by one predetermined adjusted bandwidth equal to 1 Hz based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the predetermined adjusted bandwidth, and when a current output frequency of the multiple frequencies is equal to the base frequency, the current output frequency is a last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the predetermined adjusted bandwidth, the fourth output frequency of the multiple frequencies is calculated as the second output frequency minus the predetermined adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the sweep bandwidth, the second output frequency of the multiple frequencies is calculated as the first output frequency plus the predetermined adjusted bandwidth, and when the current output frequency of the multiple frequencies is equal to the base frequency, the current output frequency is the last output frequency.

13. A method for regulating water metabolism function of cells of the animals or human, comprising the steps of: providing a system as claimed in claim 1; according to the multiple controls, the energy wave generator generating and emitting energy waves each with a corresponding energy density having a value between 0.00~7.12 by a corresponding base frequency between 100~10100 Hz to effect on bodies of animals or human so as to regulate water metabolism function of cells of the animals or human; the energy wave's frequency control mode comprising multiple fixed frequency sweep modes and multiple adjusted frequency sweep modes; the multiple adjusted frequency sweep modes being at least one sweep decreasing mode, at least one spread contract mode and/or at least one sweep increasing mode; the energy wave generator emitting energy waves to have a frequency decreasing distribution in a predetermined sweep bandwidth with an adjusted bandwidth in the sweep decreasing mode, to have a frequency increasing distribution in a predetermined sweep bandwidth with an adjusted bandwidth in the sweep increasing mode, and to have an increasing frequency and a decreasing frequency alternately in a predetermined sweep bandwidth with an adjusted bandwidth in the spread contract mode; the energy density of each energy wave being calculated by the following formula: ED=log 10 (freq.×D %×(2Width+1)×(TT)+1), wherein freq., Width, D % and TT represent the base frequency, the predetermined sweep bandwidth, an emission rate and a total time of emission in a duty cycle of the base frequency respectively.

14. The method as claimed in claim 13, wherein the multiple controls are five sets, the multiple energy wave generation periods are five sequentially from a 1st to fifth corresponding to the five sets of controls, according to the nine sets of controls, the energy wave generator sequentially emit five sets of energy waves from a 1st to fifth with corresponding five sets of energy densities between 3.17~7.03, 3.10~6.82, 1.95~7.12, 1.63~5.83 and 0.00~6.03 respectively.

15. The method as claimed in claim 14, wherein there are four non-energy periods from a first to an fourth non-energy periods sequentially between every two adjacent periods of the multiple energy wave generation periods, the energy wave generator generates various frequencies in each non-energy period and filters the various frequencies to have non-energy correspondingly.

16. The method as claimed in claim 15, wherein the total time of the first to fourth non-energy periods are 164, 290, 410 and 705 seconds respectively, the energy wave generator generates various frequencies in each non-energy period and filters the various frequencies to have non-energy.

17. The method as claimed in claim 14, wherein in the first energy wave generation period corresponding to the first set of controls, the first set of energy waves are sequentially a 1st to a 6th energy waves with a 1st to a 6th energy densities by a 1st to a 6th base frequencies respectively, the 1st energy density is between 4.12~7.03, the 2nd energy density is between 3.93~6.56, the 3rd energy density is between 3.84~6.88, the 4th energy density is between 3.71~6.28, and the 5th energy density is between 3.43~6.57, and the 6th energy density is between 3.17~6.53; in the second energy wave generation period corresponding to the second set of controls, the second set of energy waves are sequentially a 7th to a 11th energy waves with corresponding a 7th to a 11th energy densities by a 7th to a 11th base frequencies respectively, the 7th energy density is between 3.14~5.95, the 8th energy density is between 3.36~5.78, the 9th energy density is between 3.11~5.75, the 10th energy density is between 3.26~6.82, the 11th energy density is between 3.10~5.73; in the third energy wave generation period corresponding to the third set of controls, the third set of energy waves are sequentially a 12th to a 15th energy waves with a 12th to a 15th energy densities by a 12th to a 15th base frequencies respectively, the 12th energy density is between 2.08~7.12, the 13th energy density is between 2.05~6.49, the 14th energy density is between 2.19~5.55, the 15th energy density is between 1.95~6.19; in the fourth energy wave generation period corresponding to the fourth set of controls, the fourth set of energy waves are sequentially a 16th to a 19th energy waves with a 16th to a 19th energy densities by a 16th to a 19th base frequencies respectively, the 16th energy density is between 2.21~5.24, the 17th energy density is between 1.63~5.83, the 18th energy density is between 1.80~4.87; in the fifth energy wave generation period corresponding to the fifth set of controls, the fifth set of energy waves are sequentially a 19th to a 20th energy waves with a 19th to a 20th energy densities by a 19th to a 20th base frequencies respectively, the 19th energy density is between 0.00~6.03 and the 20th energy density is between 0.00~6.00.

18. The method as claimed in claim 17, wherein the controls based on the 1st, 2nd, 4th to 9th, 11th, 12th, 14th to 16th and 18th to 20th base frequencies are fixed frequency sweep modes respectively, the D %=70%, the Width=0 Hz, and the TT=45, 50, 50, 120, 120, 55, 60, 65, 70, 75, 60, 90, 90, 45 and 45 secs respectively; the control based on the 10th base frequency is sweep decreasing modes, the D %=70%, the Width=7 Hz, and the TT=64 secs respectively; the controls based on the 3rd, 12th, 13th and 17th base frequencies are spread contract modes respectively, the D %=70%, the Width=1, 7, 7 and 2 Hz, and the TT=48, 75, 75 and 90 secs respectively; the 1st to 20th base frequencies are between 9000~10100 Hz, 4900~5100 Hz, 3100~3250 Hz, 2900~3100 Hz, 2060~2200 Hz, 1950~2050 Hz, 1400~1600 Hz, 950~1100 Hz, 850~900 Hz, 750~850 Hz, 750~830 Hz, 615~650 Hz, 560~610 Hz, 500~550 Hz, 2060~2200 Hz, 220~270 Hz, 125~170 Hz, 100~150 Hz, 2060~2200 Hz and 1950~2050 Hz, respectively.

19. The method as claimed in claim 13, wherein multiple frequencies are produced and calculated by one predetermined adjusted bandwidth equal to 1 Hz based on each base frequency in each sweep decreasing mode; multiple frequencies are produced and calculated by one predetermined adjusted bandwidth equal to 1 Hz based on each base frequency in each spread contract mode; multiple frequencies are produced and calculated by one predetermined adjusted bandwidth equal to 1 Hz based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the predetermined adjusted bandwidth, and when a current output frequency of the multiple frequencies is equal to the base frequency, the current output frequency is a last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the predetermined adjusted bandwidth, the fourth output frequency of the multiple frequencies is calculated as the second output frequency minus the predetermined adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the sweep bandwidth, the second output frequency of the multiple frequencies is calculated as the first output frequency plus the predetermined adjusted bandwidth, and when the current output frequency of the multiple frequencies is equal to the base frequency, the current output frequency is the last output frequency.

* * * * *